United States Patent
Wood et al.

(10) Patent No.: US 7,073,368 B2
(45) Date of Patent: Jul. 11, 2006

(54) CALIBRATION DEVICE FOR GAS SENSORS

(75) Inventors: Roland A. Wood, Bloomington, MN (US); James Liu, Rockford, IL (US)

(73) Assignee: Honeywell International Inc., Morristown, NJ (US)

( * ) Notice: Subject to any disclaimer, the term of this patent is extended or adjusted under 35 U.S.C. 154(b) by 97 days.

(21) Appl. No.: 10/856,363

(22) Filed: May 28, 2004

(65) Prior Publication Data

US 2005/0262924 A1 Dec. 1, 2005

(51) Int. Cl.
 *G01N 27/28* (2006.01)
(52) U.S. Cl. .................................. 73/1.03; 73/1.06
(58) Field of Classification Search ................. 73/1.03, 73/1.06
See application file for complete search history.

(56) References Cited

U.S. PATENT DOCUMENTS

| 4,025,412 | A |   | 5/1977  | LaConti        |         |
| 4,123,700 | A |   | 10/1978 | LaConti et al. |         |
| 4,171,253 | A |   | 10/1979 | Nolan et al.   |         |
| 5,668,302 | A | * | 9/1997  | Finbow et al.  | 73/23.2 |
| 6,948,352 | B1| * | 9/2005  | Rabbett et al. | 73/1.04 |

| 2003/0145644 | A1 | 8/2003 | Rabbett et al. |
| 2004/0018632 | A1 | 1/2004 | Shabana et al. |

FOREIGN PATENT DOCUMENTS

| DE | 39 39 166 A1 | 5/1991 |
| GB | 2 356 708 A  | 5/2001 |
| WO | WO 99/17110  | 4/1999 |

OTHER PUBLICATIONS

Pinkerton et al. "Bottling the Hydrogen Genie", Feb./Mar. 2004, The Industrial Physicist, vol. 10, No. 1, pp. 20-23.

* cited by examiner

*Primary Examiner*—Harshad Patel
(74) *Attorney, Agent, or Firm*—Kris T. Fredrick

(57) ABSTRACT

A gas sensor includes a gas detector, a reference gas generator, and a circuit. The reference gas generator includes a heater and a gas releasing material. The gas releasing material is in proximity to the heater such that, when the heater is energized during calibration, the gas releasing material releases an overpressure of a reference gas to the gas detector and such that, when the heater is not energized, the gas releasing material releases no substantial overpressure of the reference gas to the gas detector. The circuit energizes the heater during calibration and is responsive to an output of the gas detector during the period when the gas detector is provided the reference gas so as to calibrate the gas sensor.

32 Claims, 1 Drawing Sheet

CALIBRATION DEVICE FOR GAS SENSORS

TECHNICAL FIELD OF THE INVENTION

The present invention relates to the internal generation of a reference gas that is used to calibrate a gas sensor.

BACKGROUND OF THE INVENTION

Gas sensors have been in use for some time to sense various gases such as hydrogen, oxygen, carbon monoxide, etc. One form of a gas sensor is an electrochemical cell that uses a catalytic electrode so that the gas to be detected is either oxidized or reduced with the exchange of electrons. The flow of current due to the oxidation or reduction of the gas is then detected as a measure of the concentration of the gas to be detected.

However, a known problem with gas sensors is that they lose sensitivity over time. For example, the working life of an electrochemical cell is determined by the activity of the cell's catalytic electrode that is used to detect gas within the sensor. This activity is gradually reduced over time by contaminant gases and poisons such that the sensitivity of the sensor drifts downward.

Other types of gas sensors, such as pellistor sensors, biomimetic sensors, and tin oxide sensors that may be formed as thin film, thick film, sintered or MOSFET devices, may have similar problems.

If the instrument into which the gas sensor is built is calibrated regularly, this downward sensitivity drift can be compensated for by adjusting the gain of the gas sensor, and any faulty gas sensors can be replaced immediately. However, if the instrument is in a difficult position to service, or if calibration of the gas sensor is not otherwise freely available, it is often impossible to confirm that the gas sensor is functioning correctly. Therefore, as the gas sensor reaches the end of its working life, the output of the sensing cell may be insufficient to generate an alarm condition. As a result, a situation could arise where toxic levels of gas are present, but the gas sensor is incapable of providing the requisite warning.

A substantial effort has been invested in determining a method by which the function of a gas sensor, such as an electrochemical cell, can be checked without the need for an externally generated calibration gas. For example, it has been proposed to use additional electronic components in order to check conductive pathways through the gas sensor. While such methods can uncover broken connections, they do not provide any information on the condition of the electrodes in terms of their ability to react with the gas to be detected.

When external gas sources are used, gas detectors for industrial applications are normally calibrated to correct for drift. Toxic gas detectors are normally calibrated to measure around the Occupational Exposure Level, which for most toxic gases will be less than 50 ppm, an extremely low level. Because of the difficulty in preparing gas/air mixtures at this dilution, because some toxic gases such as hydrogen sulphide and sulphur dioxide are readily absorbed by the materials used to make the calibration gas cylinder housings, and because the stability of these mixtures can be a problem, calibration gas cylinders have a limited shelf life.

For certain gases, calibration can be done using another gas to which a gas sensor is cross sensitive. Some examples are given in the following table:

| Sensor | Calibration Gas | Equivalent to |
| --- | --- | --- |
| 0 10 ppm acid gas | 10 ppm chlorine | 10 ppm acid gas |
| 0 10 ppm nitrogen dioxide | 10 ppm chlorine | 9 ppm nitrogen dioxide |
| 0 25 ppm hydrogen cyanide | 10 ppm sulphur dioxide | 28 ppm hydrogen cyanide |
| 0 10 ppm chlorine dioxide | 10 ppm chlorine | 4 ppm chlorine dioxide |
| 0 2.5 ppm phosphine | 10 ppm sulphur dioxide | 2 ppm phosphine |
| 0 1 ppm ozone | 2 ppm chlorine | 1 ppm ozone |
| 0 10 ppm hydrogen fluoride | 5 ppm hydrogen chloride | 10 ppm hydrogen fluoride |

These equivalent values may vary when electrode materials vary and filters vary.

The present invention relates to an apparatus and method for self-calibration of gas sensors.

SUMMARY OF THE INVENTION

According to one aspect of the present invention, a self-calibrating gas sensor comprises a gas detector and a reference gas generator. The reference gas generator includes a heater and a gas releasing material. The gas releasing material is in proximity to the heater such that, when the heater is energized during calibration, the gas releasing material releases an overpressure of a reference gas to the gas detector and such that, when the heater is not energized, the gas releasing material releases no substantial overpressure of the reference gas to the gas detector.

According to another aspect of the present invention, a self-calibrating gas sensor comprises a gas detector, a reference gas generator, and a circuit. The reference gas generator includes a heater and a gas releasing material. The gas releasing material is in proximity to the heater such that, when the heater is energized during calibration, the gas releasing material releases an overpressure of a reference gas to the gas detector and such that, when the heater is not energized, the gas releasing material releases no substantial overpressure of the reference gas to the gas detector. The circuit energizes the heater during calibration and calibrates the gas sensor in response to an output of the gas detector during the period when the gas detector is provided the reference gas.

According to still another aspect of the present invention, a self-calibrating gas sensor comprises a gas detector and a hydrogen generator. The gas detector comprises an electrochemical cell. The hydrogen generator includes a heater and a metal hydride. The metal hydride is in proximity to the heater such that, when the heater is energized during calibration, the metal hydride releases an overpressure of hydrogen to the gas detector and such that, when the heater is not energized, the metal hydride releases no substantial overpressure of hydrogen to the gas detector.

According to still another aspect of the present invention, a self-calibrating gas sensor comprises a gas detector, a reference gas generator, and a continuous housing. The reference gas generator includes a heater and a gas releasing material. The gas releasing material is in proximity to the heater such that, when the heater is energized during calibration, the gas releasing material releases a reference gas to the gas detector and such that, when the heater is not energized, the gas releasing material releases no substantial overpressure of the reference gas to the gas detector. The reference gas generator and the gas detector are housed within the continuous housing.

BRIEF DESCRIPTION OF THE DRAWINGS

These and other features and advantages will become more apparent from a detailed consideration of the invention when taken in conjunction with the drawings in which.

DETAILED DESCRIPTION

Figure 1:
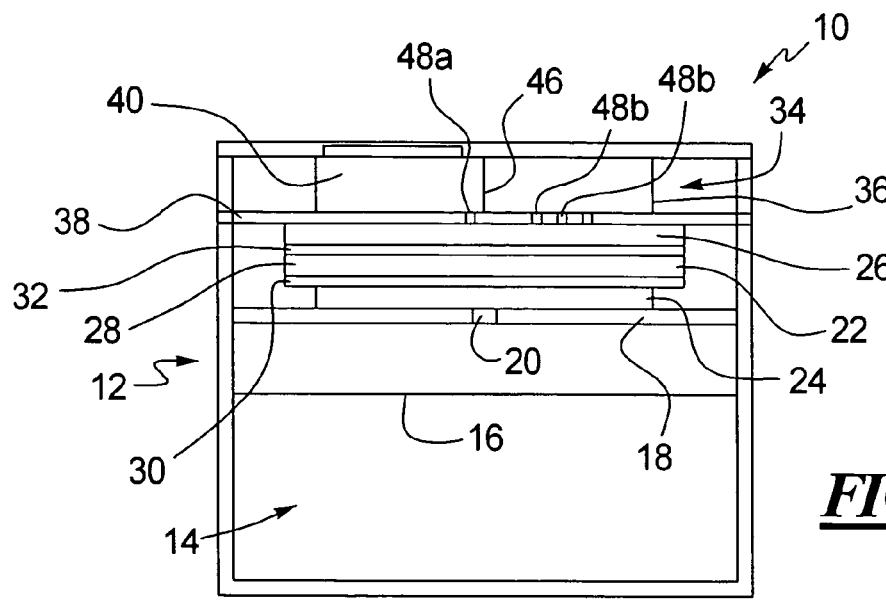
FIG. 1 illustrates a self-calibrating gas sensor according to one embodiment of the present invention.

As shown in FIG. 1, a self-calibration gas sensor 10 has a housing that, for example, may be in the form of a can 12 that is covered at its open end by a cover 13. The can 12 and the cover 13, for example, may be made of nickel plated steel. The can 12 holds a substance 14 such as water or water gel or hydrophilic oxides like silica gel in an antiseptic solution. The substance 14 provides a source of water vapor for the self-calibration gas sensor 10. As shown in FIG. 1, the substance 14 has a level 16, although the can 12 can contain more or less of the substance 14. Other materials can be used for the substance 14 depending upon the particular application temperature range for the self-calibration gas sensor 10.

A support plate 18 is provided in the can 12 above the level 16 of the substance 14. The support plate 18 has a hole 20 therethrough to permit the flow of vapor from the substance 14 through the support plate 18. The support plate 18, for example, may be a stainless steel washer.

A gas detector 22 is supported by the support plate 18. The gas detector 22, for example, may be in the form of an electrochemical cell. As such, the gas detector 22 includes lower and upper cell plates 24 and 26, a solid electrolyte membrane 28, and lower and upper catalyst electrodes 30 and 32. The lower and upper cell plates 24 and 26, for example, may be hydrophobic Teflon™ disks.

The lower cell plate 24 is sandwiched between the support plate 18 and lower catalyst electrode 30, the lower catalyst electrode 30 is sandwiched between the solid electrolyte membrane 28 and the lower cell plate 24, and the upper catalyst electrode 32 is sandwiched between the solid electrolyte membrane 28 and the upper cell plate 26. The catalyst electrodes 30 and 32, for example, may comprise an element from the group Au, Pt, Pd, Ru, Rh, Ir, Os, Ag, etc., or an alloy or mixture of the elements from this group, or porous elements of the group mixed with carbon black, or porous elements of the group mixed with carbon black and Nafion particles. The solid electrolyte membrane 28 may be Nafion or Nafion composite like Nafion/7$SiO_2$-2$P_2O_5$—$ZrO_2$, and Nafion/ZrP particles or the Sandia Polymer Electrolyte Alternative (SPEA) for higher temperature applications. The gas detector 22 may be of the type shown in one or more of U.S. Pat. Nos. 4,025,412, 4,123,700, and 4,171,253.

A reference gas generator 34 internally generates a reference gas that is provided to the gas detector 22 so that the gas detector can be self-calibrated. The reference gas generator 34 includes a reference gas generating chamber 36 and a gas diffusion control plate 38. The gas sensor 10 also includes an active charcoal filter 40. The gas diffusion control plate 38 separates the reference gas generating chamber 36 and the active charcoal filter 40 from the gas detector 22 and abuts the upper cell plate 26.

Figure 2:
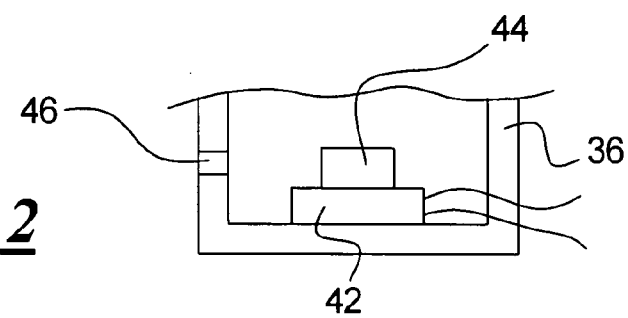
FIG. 2 shows the reference gas generator of the self-calibrating gas sensor shown in FIG. 1 in additional detail; and, FIG. 3 shows a circuit that can be sued in the self-calibration process.

As shown in FIG. 2, the reference gas generating chamber 36 houses a heater 42 and a material 44 that is in proximity to the heater 42. The material 44, when heated, produces the reference gas. For example, the material 44 may be a metal hydride that, when the heater 42 is energized, is heated to a known temperature and consequently produces a known overpressure of hydrogen. The overpressure causes the reference gas, such as hydrogen, to flow through holes 48b in the gas diffusion control plate 38 directly into to the gas detector 22.

There are many possible metal hydride materials that could be used to generate hydrogen when heated. Preferable metal hydride materials include titanium hydride, magnesium hydride and magnesium nickel hydride.

Accordingly, when the self-calibration gas sensor 10 is to be calibrated, the heater 42 is energized to heat the material 44 to a predetermined temperature and for a predetermined time that causes the material 44 to release an overpressure of the reference gas which is supplied to the gas detector 22. The gas detector 22 senses the reference gas thus generating a reference signal from the lower and upper catalyst electrodes 30 and 32. This signal is used to perform self-calibration. After such self-calibration, the heater 42 is de-energized so that the overpressure of the reference gas falls to a negligible level. Such self-calibration of the self-calibration gas sensor 10 can be intermittently repeated as desired.

As shown in FIG. 1, the can 12 forms a continuous housing that houses the gas detector 22 and the reference gas generator 34. Accordingly, in this construction of the present invention, the gas detector 22 and the reference gas generator 34 are not housed in separate and separated housings.

Figure 3:
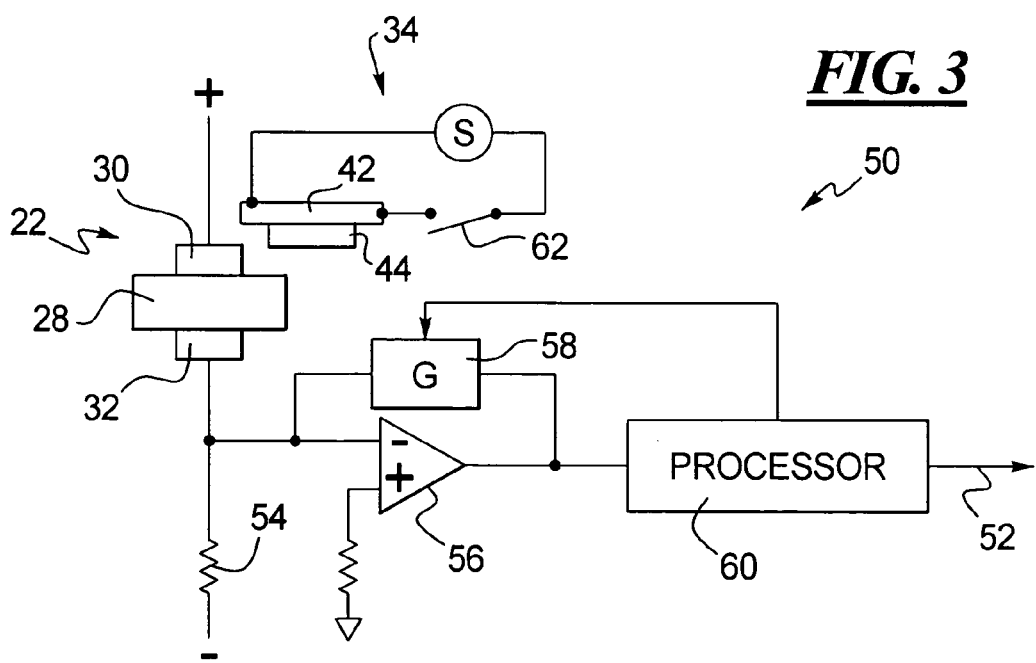

As shown in FIG. 3, a controller 50 provides an output 52 based on the gas detected by the gas detector 22 and controls the reference gas generator 34 to calibrate the gas detector 22. The output 52 may be coupled to various devices. For example, the output 52 may be coupled to an alarm indicator to produce a warning when the level of the detected gas exceeds a predetermined limit, or the output 52 may be coupled to an apparatus such as a ventilator to control the effects of the gas being detected. The self-calibration could be pre-programmed to operate twice a year or once a year. Calibration could also be initiated through pushing an external button. When self-calibration is in process, the controller 50 should provide an alarm/warning that self-calibration is being performed, and that the controller 50 may be out of function momentarily.

The lower and upper catalyst electrodes 30 and 32 are coupled between the terminals of a source through a resistor 54. The junction between the resistor 54 and the gas detector 22 is coupled to an amplifier 56 having a gain controlling element 58 in a feedback circuit around the amplifier 56. The output of the amplifier 56 is coupled to a processor 60 that provides the output 52, that controls the gain controlling element 58, and that controls a switch 62 to selectively connect a source S to the heater 42 so as to energize the reference gas generator 34.

During normal operation, the processor 60 provides the output 52 based on the output of the amplifier 56 and controls the switch 62 so that the switch 62 is open. Thus, the reference gas generator 34 is de-energized and the output 52 indicates the level of ambient gas normally being detected by the gas detector 22. This ambient gas normally being detected by the gas detector 22 enters the gas sensor 10 through one or more suitable holes (not shown) in the can 12, flows through the active charcoal filter 40, then flows through one or more holes 48a of the gas diffusion control plate 38 into the gas detector 22.

During self-calibration, the processor 60 controls the switch 62 so that the switch 62 is closed. Thus, the reference gas generator 34 is energized to produce the reference gas and to provide the reference gas to the gas detector 22 as described above. The processor 60 receives the output of the amplifier 56 and controls the gain controlling element 58 accordingly until the output of the amplifier 56 is at a desired calibration level. Accordingly, the self-calibration gas sensor 10 is calibrated.

The controller 50 may intermittently repeat the above described calibration as many times as necessary or desired. The time periods between such repeated calibrations may be periodic or aperiodic and may be of any length as desired.

The circuit 50 can be mounted as a chip or otherwise on a board or other support within the can 12. The output 52 may then be run to the exterior of the can 12.

Certain modifications of the present invention have been discussed above. Other modifications will occur to those practicing in the art of the present invention. For example, the gas detector 22 as discussed above may be an electrochemical cell. Alternatively, the gas detector 22 may be a pellistor sensor, a biomimetic sensor, and a tin oxide sensor, or other gas detector.

Moreover, FIG. 1 illustrates an embodiment of the present invention in which the can 12 forms a continuous housing that houses the gas detector 22 and the reference gas generator 34. However, the gas detector 22 and the reference gas generator 34 may instead be housed in separate and separated housings.

Furthermore, metal hydrides typically produce an over pressure of hydrogen at all temperatures, but the over pressure usually increases strongly with increasing temperature. Thus, while metal hydrides may produce a small amount of hydrogen even though they are unheated, metal hydrides can be chosen (e.g., those listed above) in which the hydrogen released at normal (unheated) temperatures is so small as to be undetectable, but in which a detectable amount is released when heated.

Also, the reference gas generating chamber 36 is preferably, although not necessarily, sealed. If sealed, it may be possible for the over pressure in the reference gas generating chamber 36 to become excessive. In this case, a suitable pressure relief valve or other compensator may be provided to maintain the over pressure below an acceptable limit.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

We claim:

1. A self-calibrating gas sensor comprising:
   a gas detector;
   a reference gas generator, wherein the reference gas generator includes a heater and a gas releasing material, wherein the gas releasing material is in proximity to the heater such that, when the heater is energized during calibration, the gas releasing material releases an overpressure of a reference gas to the gas detector and such that, when the heater is not energized, the gas releasing material releases no substantial overpressure of the reference gas to the gas detector; and,
   a filter that filters ambient gas to be detected by the gas detector.

2. The self-calibrating gas sensor of claim 1 further comprising a single can type housing, and wherein the reference gas generator and the gas detector are housed within the single can type housing.

3. The self-calibrating gas sensor of claim 1 wherein the reference gas generator includes a gas diffusion control between the heater and the gas releasing material on one side and the gas detector on the other side, and wherein the gas diffusion control controls the diffusion of the reference gas from the reference gas generator to the gas detector.

4. The self-calibrating gas sensor of claim 3 further comprising a single can type housing, and wherein the reference gas generator and the gas detector are housed within the single can type housing.

5. The self-calibrating gas sensor of claim 1 wherein the gas detector comprises an electrochemical cell.

6. The self-calibrating gas sensor of claim 5 wherein the electrochemical cell includes a hydrophobic material.

7. The self-calibrating gas sensor of claim 1 wherein the heater comprises an electrically-powered heater.

8. A self-calibrating gas sensor comprising:
   a gas detector;
   a reference gas generator, wherein the reference gas generator includes a heater and a gas releasing material, wherein the gas releasing material is in proximity to the heater such that, when the heater is energized during calibration, the gas releasing material releases an overpressure of a reference gas to the gas detector and such that, when the heater is not energized, the gas releasing material releases no substantial overpressure of the reference gas to the gas detector, and,
   a circuit that energizes the heater during calibration and that calibrates the gas sensor in response to an output of the gas detector during the period when the gas detector is provided the reference gas.

9. The self-calibrating gas sensor of claim 8 further comprising a single can type housing, and wherein the reference gas generator and the gum detector are housed within the single can type housing.

10. The self-calibrating gas sensor of claim 8 further comprising a single can type housing, and wherein the reference gas generator, the gas detector, and the circuit are housed within the single can type housing.

11. The self-calibrating gas sensor of claim 8 further including a filter that filters ambient gas to be detected by the gas detector.

12. The self-calibrating gas sensor of claim 8 wherein the reference gas generator includes a gas diffusion control between the heater and the gas releasing material on one side and the gas detector on the other side, and wherein the gas diffusion control controls the diffusion of the reference gas from the reference gas generator to the gas detector.

13. The self-calibrating gas sensor of claim 12 further comprising a single, can type housing, and wherein the reference gas generator and the gas detector are housed within the single can type housing.

14. The self-calibrating gas sensor of claim 12 further comprising a single can type housing, and wherein the reference gas generator, the gas detector, and the circuit are housed within the single can type housing.

15. The self-calibrating gas sensor of claim 12 further including a filter that filters ambient gas to be detected by the gas detector.

16. The self-calibrating gas sensor of claim 8 wherein the gas detector comprises an electrochemical cell.

17. The self-calibrating gas sensor of claim 16 wherein the electrochemical cell includes a hydrophobic material.

18. The self-calibrating gas sensor of claim 8 wherein the heater comprises an electrically-powered heater.

19. A self-calibrating gas sensor comprising:
a gas detector comprising an electrochemical cell; and,
a hydrogen generate, wherein the hydrogen generator includes a heater and a metal hydride, wherein the metal hydride is in proximity to the heater such that, when the beater is energized during calibration, the metal hydride releases an overpressure of hydrogen to the gas detector and such that, when the heater is not energized, the metal hydride releases no substantial overpressure of hydrogen to the gas detector.

20. The self-calibrating gas sensor of claim 19 further comprising a single can type housing, and wherein the hydrogen generator and the gas detector are housed within the single can type housing.

21. The melt-calibrating gas sensor of claim 19 further including a filter that filters ambient gas to be detected by the gas detector.

22. The self-calibrating gas sensor of claim 19 wherein the hydrogen generator includes a gas diffusion control between the heater and the metal hydride on one side and the gas detector on the other side, and wherein the gas diffusion control controls the diffusion of the hydrogen from the hydrogen generator to the gas detector.

23. The self-calibrating gas sensor of claim 22 further comprising a single can type housing, and wherein the hydrogen generator and the gas detector are housed within the single can type housing.

24. The self-calibrating gas sensor of claim 22 further including a filter that filters ambient gas to be detected by the gas detector.

25. The self-calibrating gas sensor of claim 19 wherein the electrochemical cell includes a hydrophobic material.

26. The self-calibrating gas sensor of claim 19 further comprising a circuit that energizes the heater during calibration and that calibrates the gas sensor in response to an output of the gas detector during the period when the gas detector is provided the hydrogen.

27. The self-calibrating gas sensor of claim 26 further comprising a single can type housing, and wherein the hydrogen generator, the gas detector, and the circuit are housed within the mingle can type housing.

28. The self-calibrating gas sensor of claim 19 wherein the heater comprises an electrically-powered heater.

29. A self-calibrating gas sensor comprising;
a gas detector;
a reference gas generator, wherein the reference gas generator includes a heater and a gas releasing material, wherein the gas releasing material is in proximity to the beater such that, when the heater is energized during calibration, the gas releasing material releases a reference gas to the gas detector and such that, when the heater is not energized the gas releasing material releases no substantial overpressure of the reference gas to the gas detector; and,
a single can type housing, wherein the reference gas generator and the gas detector are housed within the single can type housing.

30. The self-calibrating gas sensor of claim 29 further comprising a circuit that energizes the beater during calibration and that calibrates the gas sensor in response to an output of the gas detector during the period when the gas detector is provided the reference gas.

31. The self-calibrating gas sensor of claim 30 wherein the reference gas generator, the gas detector, and the circuit are housed within the single can type housing.

32. The self-calibrating gas sensor of claim 29 wherein the reference gas generator includes a gas diffusion control between the heater and the gas releasing material on one side and the gas detector on the other side, and wherein the gas diffusion control controls the diffusion of the reference gas from the reference gas generator to the gas detector.

* * * * *